(12) United States Patent
Schlüter et al.

(10) Patent No.: US 9,815,039 B2
(45) Date of Patent: Nov. 14, 2017

(54) BIOREACTOR

(75) Inventors: Thomas Schlüter, Weil im Schönbuch (DE); Uwe Heitland, Bad Oeynhausen (DE)

(73) Assignee: Bernhard Horstmann, Bad Oeynhausen (DE)

( * ) Notice: Subject to any disclaimer, the term of this patent is extended or adjusted under 35 U.S.C. 154(b) by 1325 days.

(21) Appl. No.: 12/518,046

(22) PCT Filed: Dec. 6, 2007

(86) PCT No.: PCT/DE2007/002190
§ 371 (c)(1),
(2), (4) Date: Nov. 9, 2009

(87) PCT Pub. No.: WO2008/067800
PCT Pub. Date: Jun. 12, 2008

(65) Prior Publication Data
US 2010/0317095 A1    Dec. 16, 2010

(30) Foreign Application Priority Data

Dec. 7, 2006   (DE) .................. 10 2006 058 030
Mar. 22, 2007  (DE) .................. 10 2007 014 417

(51) Int. Cl.
| | | |
|---|---|---|
| *B01F 15/06* | (2006.01) | |
| *B01F 7/00* | (2006.01) | |
| *B01F 7/04* | (2006.01) | |
| *C12M 1/107* | (2006.01) | |
| *C12M 1/06* | (2006.01) | |
| *C05F 17/02* | (2006.01) | |

(52) U.S. Cl.
CPC ........ *B01F 15/066* (2013.01); *B01F 7/00425* (2013.01); *B01F 7/04* (2013.01); *C12M 21/04* (2013.01); *C12M 23/36* (2013.01); *C12M 27/06* (2013.01); *B01F 2015/062* (2013.01); *C05F 17/0217* (2013.01); *C05F 17/0223* (2013.01)

(58) Field of Classification Search
CPC . C12M 27/06; C05F 17/0229; C05F 17/0223; C05F 17/0235; C05F 17/0217
USPC ............... 435/293.1, 290.1; 52/251, 414
See application file for complete search history.

(56) References Cited

U.S. PATENT DOCUMENTS

| | | | | |
|---|---|---|---|---|
| 2,952,588 | A * | 9/1960 | Rinderer | 435/298.2 |
| 3,594,277 | A * | 7/1971 | Mako | 435/71.1 |
| 3,771,757 | A * | 11/1973 | Black | 249/219.2 |
| 5,391,019 | A * | 2/1995 | Morgan | 405/129.55 |
| 6,451,589 | B1 * | 9/2002 | Dvorak | 435/290.1 |
| 7,659,108 | B2 * | 2/2010 | Schmid | 435/293.1 |
| 2008/0011034 | A1 * | 1/2008 | Hochrein et al. | 71/9 |

FOREIGN PATENT DOCUMENTS

| | | |
|---|---|---|
| AT | 405 185 | 6/1999 |
| DE | 44 16 521 | 1/1995 |
| WO | WO 2006/079227 | 8/2006 |

* cited by examiner

Primary Examiner — Jonathan Hurst
(74) Attorney, Agent, or Firm — Cozen O'Connor

(57) ABSTRACT

Disclosed is a bioreactor, especially a plug flow bioreactor, including an agitator running along a longitudinal axis for thoroughly mixing a dry solid biomass that is to be out-gassed in a fermentation chamber. In said bioreactor, an agitator shaft is mounted exclusively in two opposite end walls of the fermentation chamber while at least one free end of the agitator is connected to a drive unit outside the fermentation chamber.

18 Claims, 3 Drawing Sheets

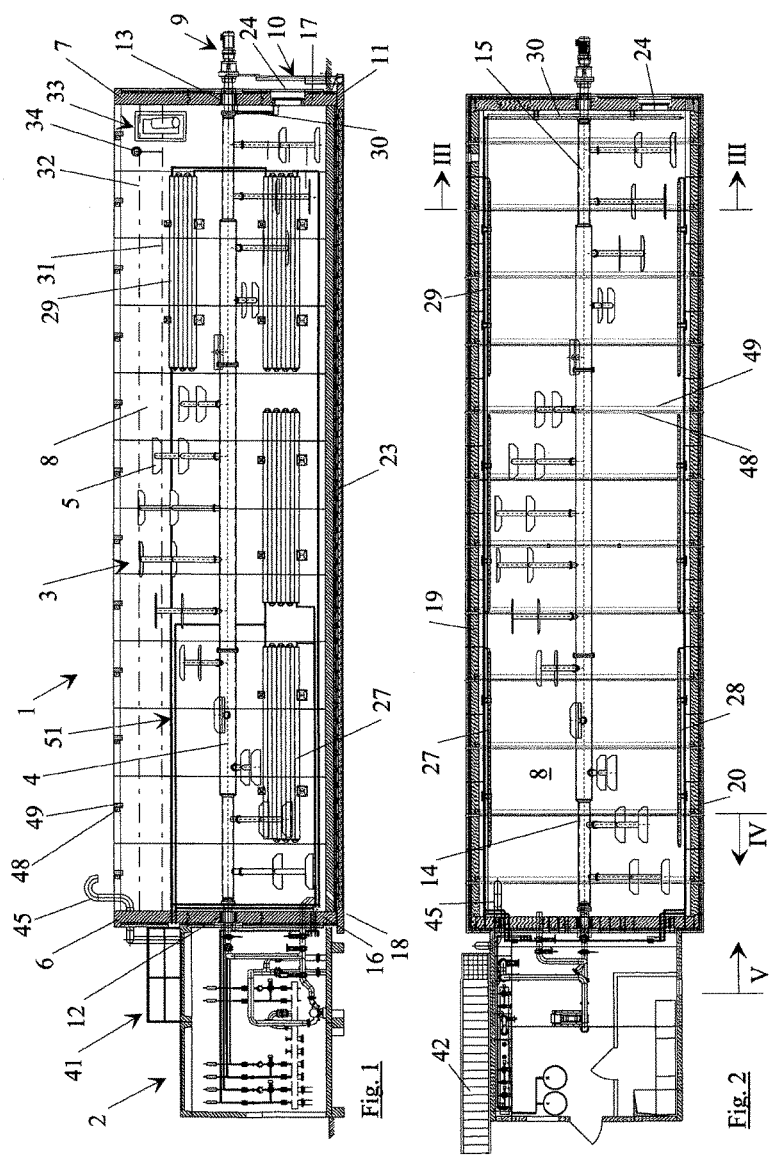

BIOREACTOR

PRIORITY CLAIM

This is a U.S. national stage of application No. PCT/DE2007/002190, filed on Dec. 6, 2007. Priority is claimed on German Application No. 10 2006 058 030.3, filed Dec. 7, 2006 and German Application No. 10 2007 014 417.4, filed Mar. 22, 2007, the contents of both of which are incorporated herein by reference.

BACKGROUND OF THE INVENTION

1. Field of the Invention

The invention relates to a bioreactor, especially a plug flow bioreactor, which has a long-shaft agitator for thoroughly mixing a biomass with a high solids content that is to be degassed in a fermentation chamber.

2. Description of the Prior Art

The use of bioreactors in biogas plants is well known and has proven effective. In this connection, bioreactors are used for the fermentation of biowaste, green waste, food waste or the like, which has a high solids content, for example, more than 40%, without the addition of liquid manure. The resulting fermentation is dry mesophilic or thermophilic fermentation at moderate temperatures, for example, 37-41° C. or 50-60° C.

In addition, a plug flow bioreactor can be continuously charged, which is equivalent to a large input of biomass to be fermented, which in turn results in a high gas yield. The agitator ensures optimal degassing and a uniform temperature distribution, and the results plug flow ensures a well-defined residence time of the substrate in the bioreactor.

Plug flow bioreactors of the type under discussion are comparatively complicated in their design and normally require a large number of additional buildings, for example, operations buildings, gas accumulators, etc.

The capital expenses of biogas plants operated in this way are correspondingly high.

SUMMARY OF THE INVENTION

Against this technical background, an objective of the invention is to develop a bioreactor that can be built simply and thus inexpensively in a short construction time and which has a high gas output and yet is very easy to maintain.

In a embodiment, a bioreactor, especially a plug flow bioreactor, having a long-shaft agitator for thoroughly mixing a biomass with a high solids content that is to be degassed in a fermentation chamber is disclosed. A shaft of the agitator is supported in two opposite end walls of the fermentation chamber and at least one free end of the agitator is connected to a drive outside the fermentation chamber.

Due to a preferably exclusive mounting of the long-shaft agitator in the end walls, undisturbed plug flow develops, which ensures uniform material throughput and uniform temperature distribution in the substrate to be degassed. Dead water at an additional center bearing of the agitator shaft is avoided, since a center bearing of this type rotates completely in the fermentation substrate.

The arrangement of the drive outside the fermentation chamber allows simple inspection of the chamber without the need for personnel to make a dangerous entrance into the chamber on a regular basis. In accordance with one embodiment of the invention, entrance of personnel into the fermentation chamber of a bioreactor thus becomes a rare occurrence.

In one embodiment of the bioreactor the torque of the drive decoupled from a rising end wall of the fermentation chamber is introduced into a foundation. This end wall can then also be correspondingly weakly dimensioned.

Alternatively, the torque of the drive, is introduced into a rising end wall of the fermentation chamber by a torque support.

Both alternatives allow safe absorption of the high drive power of about 30 kW at a torque of about 100,000 Nm without any weakening of the wall in the immediate vicinity of the opening for the bearing or the shaft due to a large number of fastening bolts, heavy-duty dowels or the like.

Furthermore, both bearings of the agitator are preferably accessible and replaceable from outside the fermentation chamber, for inspection as well as in the event of damage, naturally, after the substrate level in the fermentation chamber has been lowered sufficiently. Entrance into the fermentation chamber is therefore not necessary.

A central shaft of the agitator is preferably several axial sections of reduced diameter at each end wall. Accordingly, the bearings in the end walls can also have a small diameter, so that the end walls are weakened only slightly by the corresponding openings for the bearings.

In a bioreactor accordingly to one embodiment of the invention, the walls are segmented precast concrete units rest on continuous footings. The construction of the bioreactor with segmented precast concrete units does not require an expensive foundation but rather only the construction of cost-effective continuous footings to reduce capital expenses. The short construction time and a large degree of independence from weather contribute further to reduced capital expenses. Beyond that, especially a very high, constant concrete quality, which withstands even aggressive substrates and gases at all times, is guaranteed.

In a further embodiment of the bioreactor of the invention, the undersides of the walls have a foot with an L-shaped bend and that the foot rests on a continuous footing. Without any anchoring, a segmented precast concrete unit of this is set onto the continuous footing and aligned. If all of the precast concrete units are correctly positioned and possibly braced, a bioreactor bottom plate, which may consist of multiple layers, is constructed by casting into the space between the walls.

The use of precast concrete units provides a simple for the longitudinal walls to taper towards the top. This takes the decreasing pressure by the substrate into account, and material can thus be saved.

Moreover, the use of segmented precast concrete units, for a wall includes at least longitudinal bracing, in the form of tension rods. A mechanically stable structure is guaranteed in this way.

The mechanical stability of the bioreactor is further enhanced if opposite segments of the precast concrete units of the longitudinal walls are joined on the upper side by a tension rod placed under a tensile load and a beam placed under a compressive load. Due to this distribution to a tension rod that can be placed under a tensile load and a beam that can be placed under a compressive load, the tension rod and the beam can be designed optimally and with the appropriate material. In particular, the tension rod is made of a metal, especially a high-grade steel, and that the beam is a wooden beam that is inserted in pockets in the walls. This further reduces capital expenses.

Mechanical stability of the bioreactor allows the fermentation chamber to be covered by a roof that serves as a gas accumulator designed with a semicircular cross section. This avoids an external gas accumulator. Furthermore, there is no need for a heavy and expensive concrete roof that seals the fermentation chamber at the top. In accordance with one embodiment of the invention, it is possible, for the roof to be constructed in the manner of an inflatable hall, in particular, for it to be formed by a sheet, and for it to be removed during operation. Inspection work is thus greatly simplified, and, when necessary, the long-shaft agitator can be removed and restored without any trouble when the roof has been removed. In particular, these measures also make it possible largely to avoid dangerous work inside a closed fermentation chamber.

Finally, the fermentation chamber is covered by a net. A net of this type serves effectively for the colonization of sulfur bacteria, which are useful in the fermentation processes in a bioreactor of the aforementioned type. In addition, the net, which is supported on the tension rods and/or stays, supports a membranous sheet on the underside of the gas accumulator and prevents the sheet from sagging into the fermentation chamber.

BRIEF DESCRIPTION OF THE DRAWINGS

The invention is explained in greater detail below with reference to the figures, which show schematic representations of a specific embodiment of the invention.

FIG. 1 is a bioreactor;
FIG. 2 is a partial section of the bioreactor of FIG. 1 in a top view.

DETAILED DESCRIPTION OF THE PREFERRED EMBODIMENTS

Figure 3:
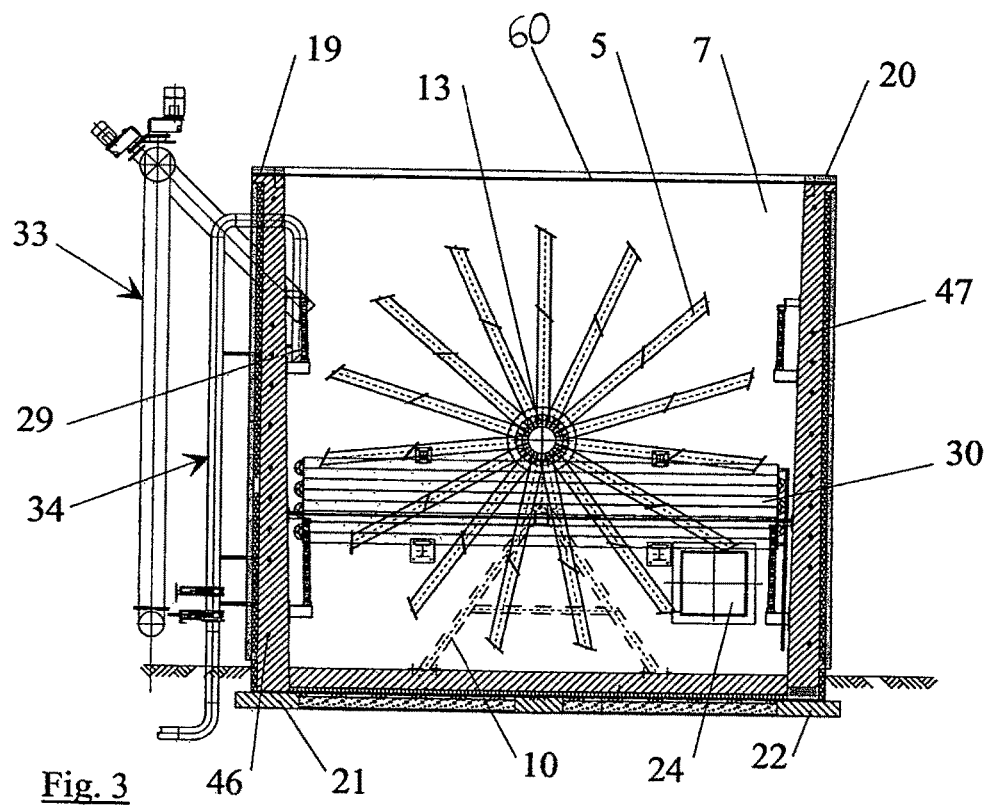
FIG. 3 is a section along line III in FIG. 2.

FIG. 1 is an off-center longitudinal section through a bioreactor 1 of one embodiment of the invention with an operations building 2 is connected to an end face of the bioreactor 1. The bioreactor is designed as a plug flow bioreactor with a long-shaft agitator 3, which has a central shaft 4 with a plurality of blades 5 that rotate spirally in the axial direction. The shaft 4 of the agitator 3 is supported on bearings exclusively in the two opposite end walls 6, 7. A center bearing is preferably deliberately dispensed with.

The shaft 4 passes through the wall 7 on the end opposite the operations building 2 and is connected to an electric motor drive 9 outside the fermentation chamber 8. The torque produced by the drive 9 is introduced into a foundation 11 via a triangular support structure 10 decoupled from the end wall 7 of the fermentation chamber 8, (see also FIG. 3).

The shaft 4, which is supported in the bearings 12, 13 in the walls 6, 7, is preferably divided into five axial sections. The two end sections 14, 15 of the shaft 4 shown in FIG. 2 have a reduced diameter relative to the three middle sections. The bearings 12, 13 of the shaft 4, as well as the drive 9, are accessible and replaceable from outside the fermentation chamber 8.

FIG. 1 also shows that the end walls 6, 7, which in one embodiment, have essentially constant material thickness over their height, are each preferably formed by at least three horizontally subdivided precast concrete units. The lowermost precast concrete units 16, 17 preferably have L-shaped feet by which they are supported on the foundation or continuous footings 11, 18.

Similarly to the end walls 6, 7, the longitudinal walls 19, 20 shown in FIG. 2 are formed by precast concrete units, which likewise are preferably horizontally and vertically segmented. The lowermost rows of the precast concrete units of the longitudinal walls are likewise supported on continuous footings 21, 22 as shown in FIG. 3. When at least the lowermost rows of the precast concrete units have been placed so that they are positioned on the continuous footings 11, 18, 21, 22, a multilayer floor 23 that joins the walls 6, 7; 19, 20 is cast.

The end walls 6, 7 preferably have an essentially constant cross section over their height. Like the end walls 6, 7, the longitudinal walls 19, 20 are also made to seal the fermentation chamber 8 and have an insulating layer that faces outward and is covered by a plate.

Figure 4:
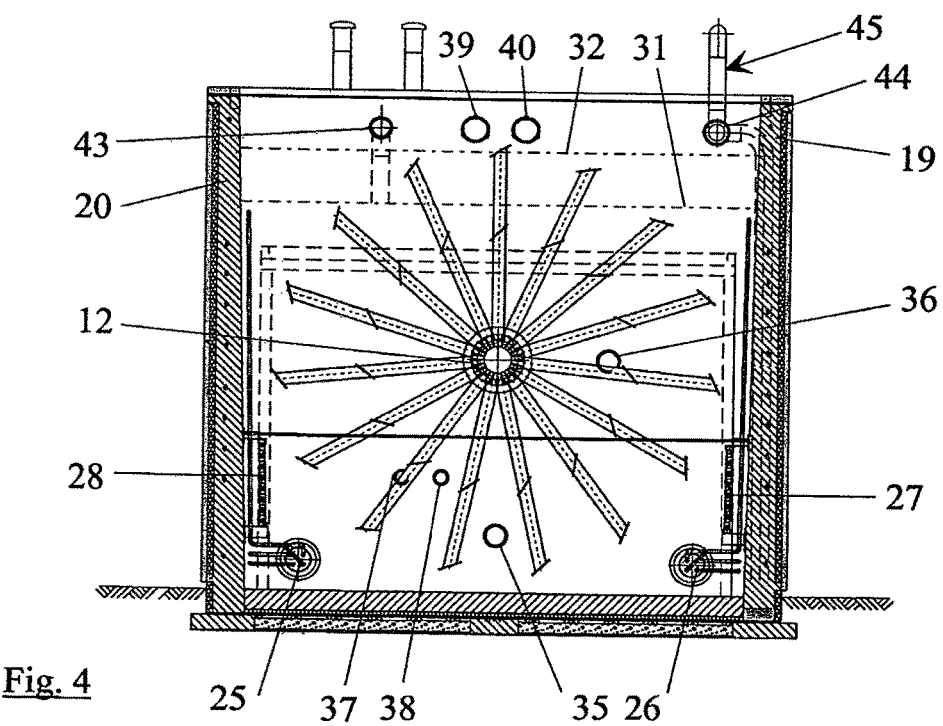
FIG. 4 is a section along line IV in FIG. 2.

In addition to an opening for holding the bearing 13, the end wall 7 preferably has one opening 24 for a manhole. The wall 6 is provided with a number of other openings, through which a variety of different conduction systems can be passed into the operations room 2. For example, as shown in FIG. 4, openings 25, 26 in end wall 7 are preferably lined with fiber-cement sheaths and carry out the feed and return of a plurality of heaters 27 to 30 installed on the longitudinal walls 19, 20 that are vented via pipelines 51 that pass through the wall 6 to the outside.

Heaters 29 are installed at a level below a minimum level 31 of the substrate introduced into the fermentation chamber 8. This minimum level 31 is indicated by a dot-dash line. The upper level 32, which is also indicated by a dot-dash line, lies above the upwardly directed blades 5 of the agitator 3.

In one embodiment, the biomass is introduced through a supply line 33 in the longitudinal wall 19. In the immediate vicinity of this supply line 33, liquid substrate is introduced through another supply line 34. Accordingly, at the other end of the bioreactor 1, a lower substrate outlet 35 and an upper substrate outlet 36 are provided in the wall 6.shown in FIG. 4.

Openings 37, 38 in the wall 6 allow measurements of the level of filling and/or the temperature. Openings 39, 40 enclosed by transparent glass make it possible to look into the fermentation chamber 8 from a work platform 41 on the roof of the operations building 2, which can be reached by stairs 42.

Another opening 43 serves the purpose of negative and positive pressure safety, and still another opening 44 formed above the upper level 32 serves for the passage of a pipe system 45 for the removal of gas.

The longitudinal walls 19, 20 have a cross section that preferably tapers towards the top as shown in FIGS. 3 and 4. To obtain good mechanical bracing of the precast concrete units, the two longitudinal walls 19, 20 have a plurality of longitudinal stays 46, 47, configured as tension rods, for longitudinally bracing the lateral walls 19, 20.

Figure 5:
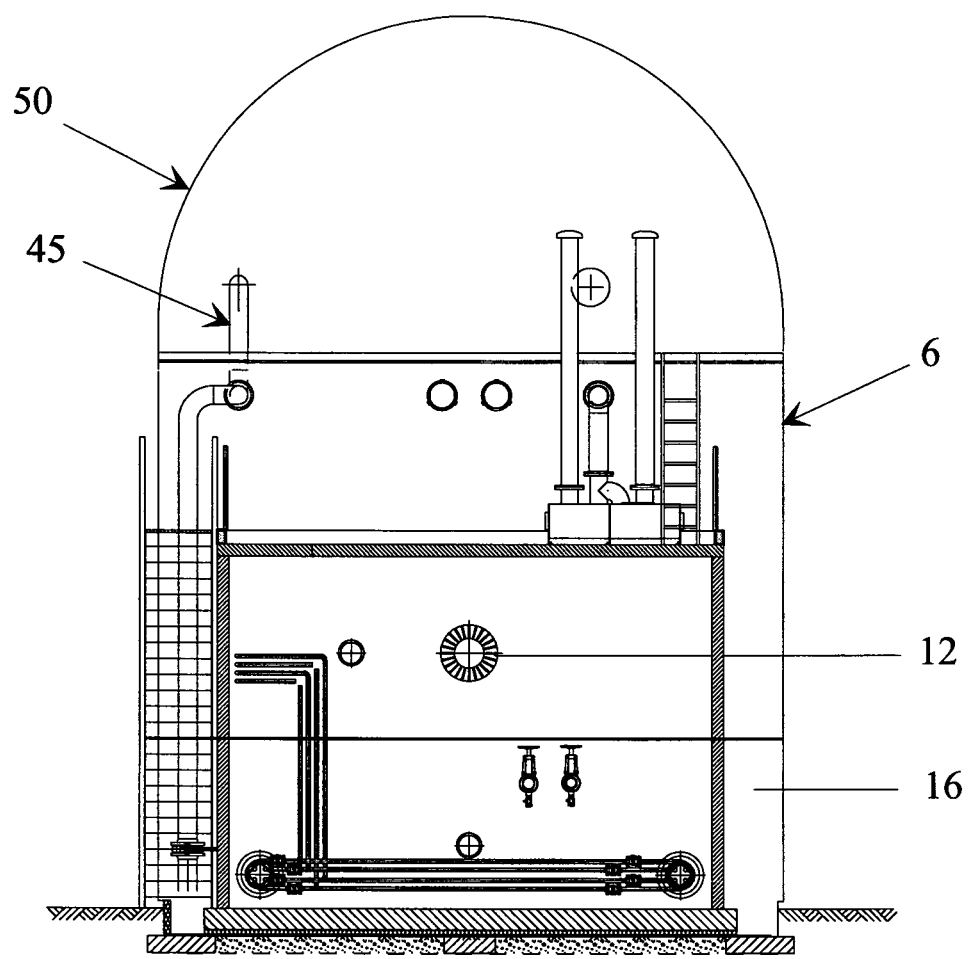
FIG. 5 is a section along line V in FIG. 2.

In addition, opposite segments of precast concrete units of the two longitudinal walls 19, 20 are joined on the upper side by a tension rod 48 that is preferably made of metal, especially high-grade steel, that can be placed especially under a tensile load and by a wooden beam 49 that can be placed under a compressive load and is merely inserted in pockets of the segments of the longitudinal walls 19, 20. This ensures that the walls 6, 7, 19, 20 have sufficient stability to allow a roof 50 to be placed on them. The roof 50 shown in FIG. 5 is designed with a semicircular cross section and is provided as a gas accumulator, from which the gas formed in the fermentation chamber 8 can be removed through the pipe system 45, which opens above the upper level 32 of the substrate.

The roof 50 is preferably formed in the manner of an inflatable hall, whose gas-tight sheet can also be removed during operation, so that the fermentation chamber 8 is practically freely accessible from above, for example, for inspection work.

A net 60 that serves as a growth surface for sulfur bacteria and thus allows effective internal desulfurization is preferably also provided between the roof 50 and the fermentation chamber 8. In addition, the net, supported on the tension rods 48 and/or the beam 49, prevents a membranous sheet on the underside of the gas accumulator from sagging into the fermentation chamber 8.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A plug flow bioreactor, comprising:
   a fermentation chamber having a first end wall and a second end wall opposite the first end wall;
   a long-shaft agitator configured to mix a biomass with a high solids content to degas the biomass in the fermentation chamber, the long-shaft agitator comprising a central shaft divided into a plurality of axial sections including a first axial end section and a second axial end section partially within the fermentation chamber, the first axial end section and the second axial end section being supported, in part, by the two opposite end walls of the fermentation chamber to exclusively support the long-shaft agitator in the two opposite end walls of the fermentation chamber;
   a plurality of blades that extend radially from the long shaft agitator, wherein at least one respective blade is affixed to at least some of the plurality of axial sections of the long-shaft agitator, including to the first axial end section and the second axial end section;
   a drive outside the fermentation chamber coupled to at least one free end of the long-shaft agitator, the drive being positioned along a longitudinal axis of the agitator;
   a foundation supporting the fermentation chamber; and
   a support separate from the drive, the support being cupid to the drive and to the foundation to support the drive outside of the fermentation chamber and to introduce torque of the drive into the foundation,
   wherein the first axial end section and the second axial end section of the long-shaft agitator arranged at the opposite end walls of the fermentation chamber each form respective outer diameters of the long-shaft agitator within the fermentation chamber that are smaller than an outer diameter of a section of the long-shaft agitator arranged between the first axial end section and the second axial end section of the long-shaft agitator.

2. The plug flow bioreactor according to claim 1, further comprising a bearing in each of the two opposite end walls of the fermentation chamber, the bearings configured to support the long shaft agitator.

3. The plug flow bioreactor according to claim 2, wherein the bearings of the long-shaft agitator are configured to be accessible and replaceable from the outside of the fermentation chamber.

4. The plug flow bioreactor according to claim 1, further comprising:
   a pair longitudinal walls connecting the first and second end walls,
   wherein the first end wall, the second end all, and the pair of longitudinal walls each comprise a plurality of segmented precast concrete units configured to rest on continuous footings.

5. The plug flow bioreactor according to claim 4, wherein the walls have a foot with an L-shaped bend configured to rest on the continuous footing.

6. The plug flow bioreactor according to claim 4, wherein the walls taper towards a top opposite the footing.

7. The plug flow bioreactor according to claim 4, wherein the side walls further comprise longitudinal bracing.

8. The plug flow bioreactor according to claim 4, further comprising:
   a tension rod configured to join opposite segments of the precast concrete units of the longitudinal walls; and
   a beam configured to join the opposite segments of the precast concrete units of the longitudinal walls,
   wherein the beam can bear a compressive load.

9. The plug flow bioreactor according to claim 8, wherein the tension rod comprises metal.

10. The plug flow bioreactor according to claim 8, wherein the beam comprises wood.

11. The plug flow bioreactor according to claim 8, further comprising a roof to cover the fermentation chamber, the roof being configured to serve a gas accumulator, the roof having a semicircular cross section.

12. The plug flow bioreactor according to claim 11, wherein the roof is constructed in the manner of an inflatable hall.

13. The plug flow bioreactor according to claim 11, wherein the roof comprises a removeable sheet.

14. The plug flow bioreactor according to claim 11, further comprising a net configured to cover the fermentation chamber.

15. The plug flow bioreactor according to claim 14, further comprising:
   a membranous sheet on the underside of the gas accumulator; and
   tension rods and supports to support the net.

16. The plug flow bioreactor according to claim 11, wherein the roof is configured to be removed from the fermentation chamber during operation.

17. The plug flow bioreactor according to claim 1, wherein the support is triangular.

18. The plug flow bioreactor according to claim 1, wherein at least one of the plurality of blades is affixed to each of the plurality of axial sections.

* * * * *